(12) United States Patent  (10) Patent No.: US 7,491,959 B2
Ogawa et al.  (45) Date of Patent: Feb. 17, 2009

(54) DEFECT INSPECTION APPARATUS

(75) Inventors: Riki Ogawa, Kawasaki (JP); Soichiro Mitsui, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 197 days.

(21) Appl. No.: 11/526,638

(22) Filed: Sep. 26, 2006

(65) Prior Publication Data

US 2007/0070334 A1 Mar. 29, 2007

(30) Foreign Application Priority Data

Sep. 29, 2005 (JP) ............................. 2005-284395

(51) Int. Cl.
*G01V 8/00* (2006.01)
(52) U.S. Cl. ............................ 250/559.45; 250/559.11; 250/237 R; 356/237.5
(58) Field of Classification Search ............. 250/237 R, 250/559.45, 559.11; 356/237.5
See application file for complete search history.

(56) References Cited

U.S. PATENT DOCUMENTS

| 3,963,354 | A | * | 6/1976 | Feldman et al. ............. 356/394 |
| 4,958,083 | A | * | 9/1990 | Sakamoto ................ 250/559.41 |
| 5,098,191 | A | * | 3/1992 | Noguchi et al. ............ 356/394 |
| 5,235,400 | A | * | 8/1993 | Terasawa et al. .......... 356/237.5 |
| 5,892,579 | A | * | 4/1999 | Elyasaf et al. ............ 356/239.8 |
| 6,175,645 | B1 | * | 1/2001 | Elyasaf et al. .............. 382/147 |
| 6,665,065 | B1 | * | 12/2003 | Phan et al. ................ 356/237.1 |
| 6,930,770 | B2 | * | 8/2005 | Elyasaf et al. ............ 356/237.1 |
| 2004/0252296 | A1 | * | 12/2004 | Tojo et al. ................ 356/237.5 |
| 2005/0002020 | A1 | * | 1/2005 | Inoue et al. ............... 356/237.1 |
| 2006/0082782 | A1 | | 4/2006 | Ogawa et al. |
| 2006/0087649 | A1 | | 4/2006 | Ogawa et al. |

FOREIGN PATENT DOCUMENTS

JP  10-177246  6/1998
JP  2004-354088  12/2004

OTHER PUBLICATIONS

Japanese Patent Office Action entitled "Notice of Reason for Rejection" mailed May 27, 2008, in corresponding Japanese Patent Application No. 2005-284395.

* cited by examiner

*Primary Examiner*—Stephen Yam
(74) *Attorney, Agent, or Firm*—Finnegan, Henderson, Farabow, Garrett & Dunner, L.L.P.

(57) ABSTRACT

A defect inspection apparatus includes an illumination optical system which sets a transmission illumination region and a reflection illumination region on an inspection target surface of a mask, first and second imaging units having first and second visual fields which are set on the inspection target surface, an imaging optical system that provides images, which are present on the first and second visual fields, on the first and second imaging units, a defect detection unit which detects a defect of the mask on the basis of the images provided on the first and second imaging units, and a control unit which controls a positional relationship between setting positions of the transmission illumination region and the reflection illumination region and setting positions of the first and second visual fields.

12 Claims, 4 Drawing Sheets

DEFECT INSPECTION APPARATUS

CROSS-REFERENCE TO RELATED APPLICATIONS

This application is based upon and claims the benefit of priority from prior Japanese Patent Application No. 2005-284395, filed Sep. 29, 2005, the entire contents of which are incorporated herein by reference.

BACKGROUND OF THE INVENTION

1. Field of the Invention

The present invention relates to a defect inspection apparatus which inspects a defect of a mask.

2. Description of the Related Art

With an increase in integration density of a semiconductor device such as an LSI, a mask pattern that is formed on a mask, such as a reticle, has become finer. Accordingly, a defect inspection apparatus for a mask pattern is required to have higher performance. There has been proposed a defect inspection apparatus which detects a defect by acquiring an image of a mask pattern by means of an imaging device such as a CCD or a line sensor, and comparing the acquired image with a reference image (see, e.g. JP-A 10-177246 (KOKAI)).

Normally, when an image of a mask pattern is acquired, both transmission illumination and reflection illumination are used. The transmission illumination and reflection illumination have merits and demerits. By using both the transmission illumination and reflection illumination, their characteristics are made complementary.

However, if the positions of a transmission illumination region and a reflection illumination region are fixed, a desired image, in some cases, cannot be obtained. For example, an optical system has aberration and distortion. Although an image with high precision is obtained at a center of a visual field of an objective lens, but an image with high precision is hardly obtained at positions away from the center of the visual field of the objective lens. Consequently, if the transmission illumination region is positioned at the center of the visual field of the objective lens, the precision of a transmission illumination image is enhanced but the precision of a reflection illumination image is degraded. Conversely, if the reflection illumination region is positioned at the center of the visual field of the objective lens, the precision of a reflection illumination image is enhanced but the precision of a transmission illumination image is degraded.

As described above, if the positions of the transmission illumination region and reflection illumination region are fixed, such a problem arises that a desired image can hardly be acquired with high precision and a defect inspection cannot be performed with high precision.

BRIEF SUMMARY OF THE INVENTION

According to an aspect of the present invention, there is provided a defect inspection apparatus comprising: an illumination optical system which sets a transmission illumination region and a reflection illumination region on an inspection target surface of a mask; first and second imaging units having first and second visual fields which are set on the inspection target surface; an imaging optical system that provides images, which are present on the first and second visual fields, on the first and second imaging units; a defect detection unit which detects a defect of the mask on the basis of the images provided on the first and second imaging units; and a control unit which controls a positional relationship between setting positions of the transmission illumination region and the reflection illumination region and setting positions of the first and second visual fields.

DETAILED DESCRIPTION OF THE INVENTION

An embodiment of the present invention will now be described with reference to the accompanying drawings.

Figure 1:
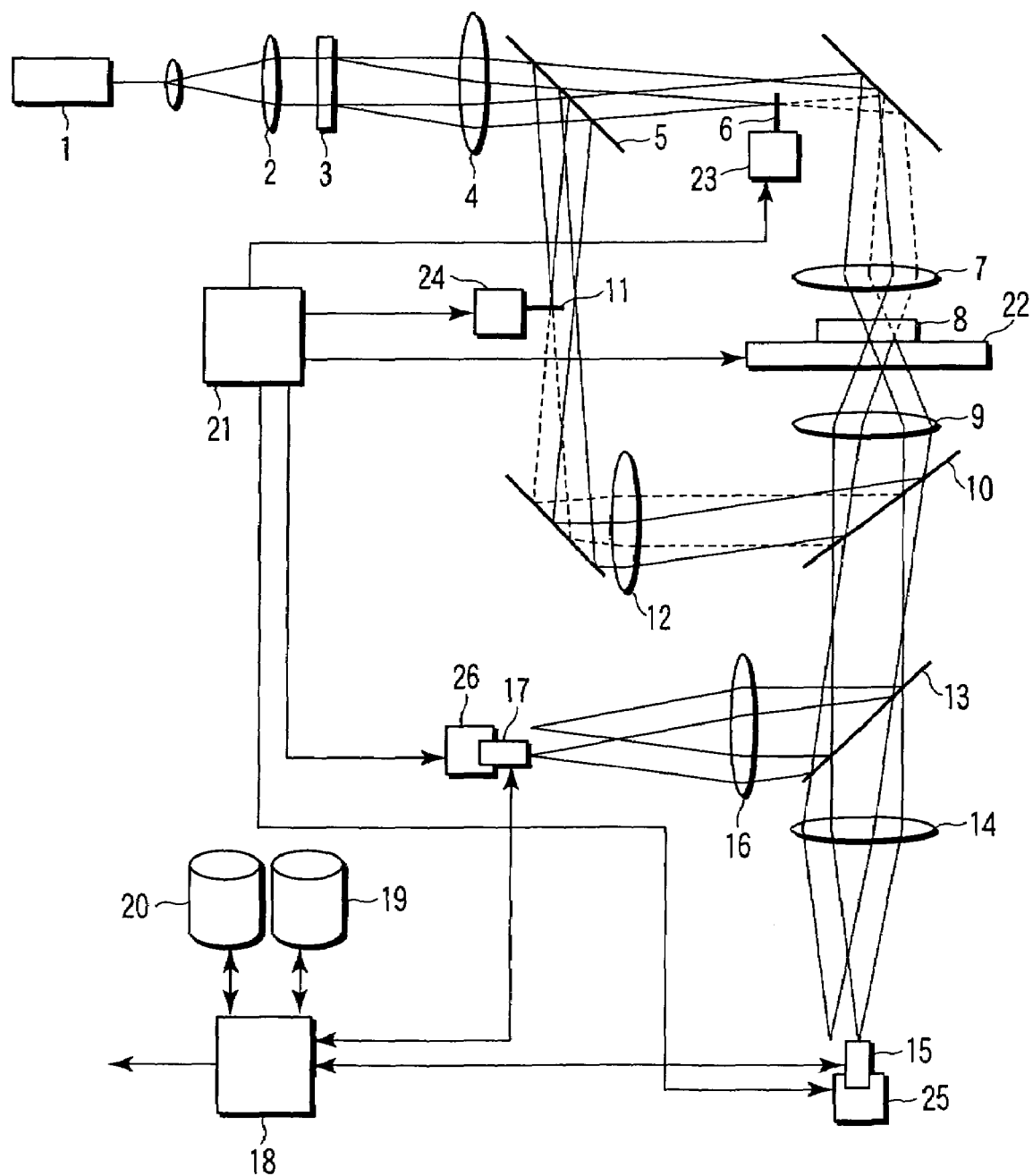
FIG. 1 schematically shows an example of the structure of a defect inspection apparatus according to an embodiment of the present invention.

FIG. 1 schematically shows an example of the structure of a defect inspection apparatus according to an embodiment of the present invention.

Light (e.g. a laser beam), which is emitted from a light source 1, is extended by a beam expander 2 and is converted to an area light source by an optical integrator 3. A fly-eye lens or a diffusion plate, for instance, is usable as the optical integrator 3. Light from the optical integrator 3 is Koehler-illuminated by a collimator 4 onto the position of a diaphragm 6 for transmission illumination and the position of a diaphragm 11 for reflection illumination. A beam splitter 5 is disposed on a rear side of the collimator 4. The light incident on the beam splitter 5 is separated into transmission illumination light and reflection illumination light.

The transmission illumination light, which is separated by the beam splitter 5, is Koehler-illuminated on the position of the diaphragm 6 for transmission illumination, as described above. The diaphragm 6 is disposed at a conjugate position with respect to the position of a pattern formation surface (an inspection target surface) of a mask 8 to be inspected (e.g. a photomask such as a reticle). The position of the diaphragm 6 is movable by a diaphragm driving mechanism 23 which is composed of, e.g. a pulse motor. By controlling the position of the diaphragm 6 by the diaphragm driving mechanism 23, a transmission illumination region is set on the pattern formation surface of the mask 8 that is disposed on a stage 22.

Light, which has passed through the diaphragm 6, is Koehler-illuminated on the pattern formation surface of the mask 8 by a condenser lens 7. The mask 8 is configured such that a pattern for an LSI is formed on a glass substrate. The illumination light reaches the pattern formation surface through the glass substrate. Thus, the condenser lens 7, which is to be used, is chosen by taking the thickness of the glass substrate into account. Since the pattern formation surface of the mask 8 is disposed at a conjugate position with respect to the position of the diaphragm 6, a transmission illumination region, which is adjusted by the diaphragm 6, is set on the pattern formation surface.

The reflection illumination light, which is separated by the beam splitter 5, is Koehler-illuminated on the position of the diaphragm 11 for reflection illumination. The diaphragm 11 is disposed at a conjugate position with respect to the position of the pattern formation surface of the mask 8. The position of the diaphragm 11 is movable by a diaphragm driving mechanism 24 which is composed of, e.g. a pulse motor. By controlling the position of the diaphragm 11 by the diaphragm driving mechanism 24, a reflection illumination region is set on the pattern formation surface of the mask 8 that is disposed on the stage 22.

Light, which has passed through the diaphragm 11, is Koehler-illuminated on the pattern formation surface of the mask 8 by a collimator 12 and an objective lens 9. A beam splitter 10 is disposed between the collimator 12 and the objective lens 9. Reflective light from the beam splitter 10 reaches the pattern formation surface of the mask 8 via the objective lens 9. Since the pattern formation surface of the mask 8 is disposed at a conjugate position with respect to the position of the diaphragm 11, a reflection illumination region, which is adjusted by the diaphragm 11, is set on the pattern formation surface.

The above-described beam expander 2, optical integrator 3, collimator 4, beam splitter 5, diaphragm 6 and condenser lens 7 constitute an illumination optical system for setting a transmission illumination region. The beam expander 2, optical integrator 3, collimator 4, beam splitter 5, diaphragm 11, collimator 12, beam splitter 10 and objective lens 9 constitute an illumination optical system for setting a reflection illumination region. The above-described diaphragm driving mechanisms 23 and 24 constitute an illumination region position control unit which controls the positions of the transmission illumination region and reflection illumination region on the pattern formation surface (inspection target surface) of the mask 8.

Light from the transmission illumination region of the mask 8, that is, image light corresponding to the pattern included in the transmission illumination region, reaches a beam splitter 13 via the objective lens 9. Similarly, light from the reflection illumination region of the mask 8, that is, image light corresponding to the pattern included in the reflection illumination region, reaches the beam splitter 13 via the objective lens 9.

The image light, which has reached the beam splitter 13, is separated into transmission light and reflection light by the beam splitter 13. Of the transmission light emerging from the beam splitter 13, a light component coming from the transmission illumination region of the mask 8 is imaged on an imaging sensor (imaging unit) 15 via an imaging lens 14, but a light component coming from the reflection illumination region of the mask 8 is not imaged on the imaging sensor 15.

In addition, of the reflection light reflected by the beam splitter 13, a light component coming from the reflection illumination region of the mask 8 is imaged on an imaging sensor (imaging unit) 17 via an imaging lens 16, but a light component coming from the transmission illumination region of the mask 8 is not imaged on the imaging sensor 17.

The imaging sensor 15 is movable by an imaging sensor driving mechanism 25 which is composed of, e.g. a pulse motor. By controlling the position of the imaging sensor 15 by the imaging sensor driving mechanism 25, the light from the transmission illumination region of the mask 8 can be imaged on the imaging sensor 15, as described above. In other words, by controlling the position of the imaging sensor 15 by the imaging sensor driving mechanism 25, the position of a visual field of the imaging sensor 15 on the pattern formation surface of the mask 8 is adjusted. As a result, on the pattern formation surface of the mask 8, the position of the visual field of the imaging sensor 15 can be made to correspond to the position of the transmission illumination region.

The imaging sensor 17 is movable by an imaging sensor driving mechanism 26 which is composed of, e.g. a pulse motor. By controlling the position of the imaging sensor 17 by the imaging sensor driving mechanism 26, the light from the reflection illumination region of the mask 8 can be imaged on the imaging sensor 17, as described above. In other words, by controlling the position of the imaging sensor 17 by the imaging sensor driving mechanism 26, the position of a visual field of the imaging sensor 17 on the pattern formation surface of the mask 8 is adjusted. As a result, on the pattern formation surface of the mask 8, the position of the visual field of the imaging sensor 17 can be made to correspond to the position of the reflection illumination region.

The above-described objective lens 9, beam splitter 13 and imaging lens 14 constitute an imaging optical system for providing an image of the transmission illumination region on the imaging sensor 15. The objective lens 9, beam splitter 13 and imaging lens 16 constitute an imaging optical system for providing an image of the reflection illumination region on the imaging sensor 17. The above-described imaging sensor driving mechanisms 25 and 26 constitute a visual field position control unit which controls the positions of the visual fields of the imaging sensors 15 and 17 on the pattern formation surface (inspection target surface) of the mask 8.

A computer 21 is connected to the above-described diaphragm driving mechanisms 23 and 24, the imaging sensor driving mechanisms 25 and 26 and the stage 22 which scans the mask 8. The operations of these components are controlled by the computer 21. The diaphragm driving mechanisms 23 and 24 and the imaging sensor driving mechanisms 25 and 26 are automatically controlled by the computer 21. Thereby, on the pattern formation surface of the mask 8, the position of the visual field of the imaging sensor 15 can automatically be made to correspond to the position of the transmission illumination region, and the position of the visual field of the imaging sensor 17 can automatically be made to correspond to the position of the reflection illumination region.

Image data of an image (transmission image) of the transmission illumination region, which is formed on the imaging sensor 15, is sent to a comparison unit 18 and is compared with reference image data of a reference transmission image which is prestored in a memory unit 19. Similarly, image data of an image (reflection image) of the reflection illumination region, which is formed on the imaging sensor 17, is sent to the comparison unit 18 and is compared with reference image data of a reference reflection image which is prestored in a memory unit 20. Based on comparison results that are thus obtained, a defect on the pattern formation surface of the mask 8 is detected. The detection of a defect may be performed by the comparison unit 18 or by the computer 21.

FIG. 2 to FIG. 6 show the positional relationships between the setting positions of the transmission illumination region and reflection illumination region, on one hand, which are controlled by the diaphragm driving mechanisms 23 and 24, and the setting positions of the visual fields of the imaging sensors 15 and 17, on the other hand, which are controlled by the imaging sensor driving mechanisms 25 and 26.

In FIG. 2 to FIG. 6, reference numeral 100 denotes an objective visual field (i.e. a visual field on the pattern formation surface of the mask 8, which is defined by the objective lens 9); numeral 101 a transmission visual field (i.e. a visual field of the imaging sensor 15 on the pattern formation surface); numeral 102 a reflection visual field (i.e. a visual field of the imaging sensor 17 on the pattern formation surface); 111 a transmission illumination region on the pattern formation surface; and 112 a reflection illumination region on the pattern formation surface. As shown in FIG. 2 to FIG. 6, the transmission visual field 101 and the reflection visual field 102 are spaced apart. The transmission illumination region 111 and the reflection illumination region 112 are spaced apart. The transmission visual field 101 is positioned within the transmission illumination region 111, and the reflection visual field 102 is positioned within the reflection illumination region 112.

Figure 2:
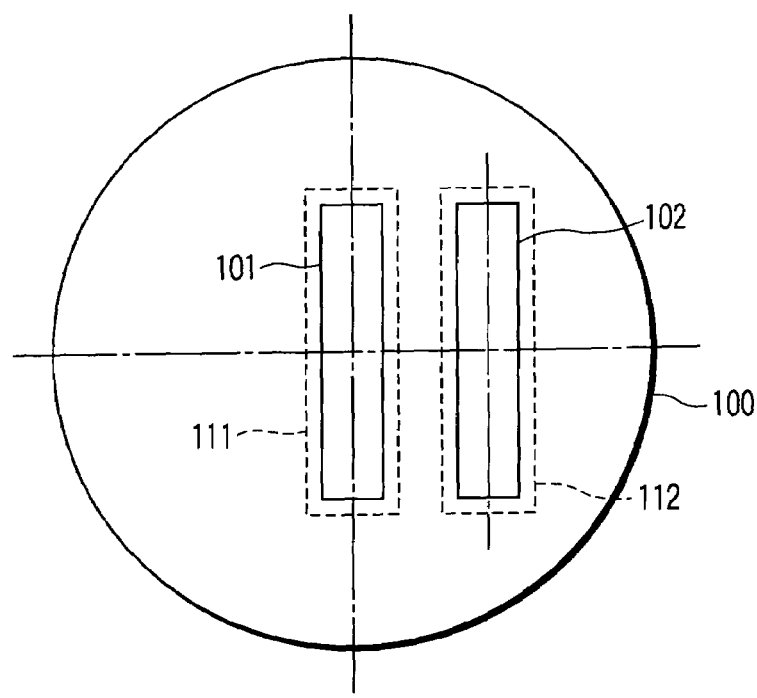
FIG. 2 shows an example of the positional relationship between the setting positions of a transmission illumination region and a reflection illumination region, on one hand, and the setting positions of visual fields of imaging sensors, on the other hand.

FIG. 2 shows a position control state with priority on transmission. The center axis of the transmission visual field 101 agrees with the center axis of the objective visual field 100. In normal defect inspections, in usual cases, the transmission image is mainly used and the reflection image is used as an auxiliary. Thus, if the transmission image is to be used as a main and the precision in detection of the transmission image is to be enhanced, the position setting state as shown in FIG. 2 is effective.

Figure 3:
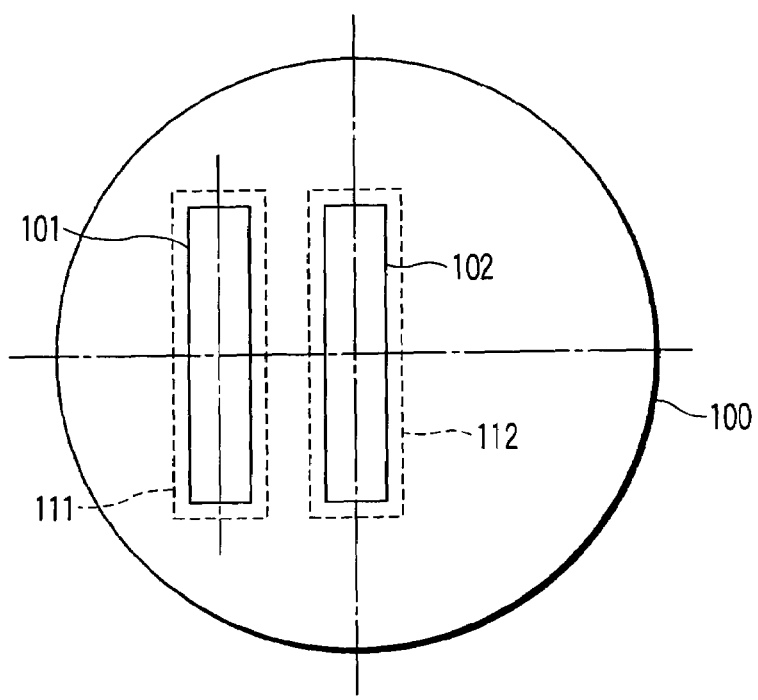
FIG. 3 shows another example of the positional relationship between the setting positions of the transmission illumination region and reflection illumination region, on one hand, and the setting positions of the visual fields of the imaging sensors, on the other hand.

FIG. 3 shows a position control state with priority on reflection. The center axis of the reflection visual field 102 agrees with the center axis of the objective visual field 100. The reflection image is suited to detection of foreign matter such as dust. Thus, if foreign matter such as dust is to be mainly detected and the precision in detection of the reflection image is to be enhanced, the position setting state as shown in FIG. 3 is effective.

Figure 4:
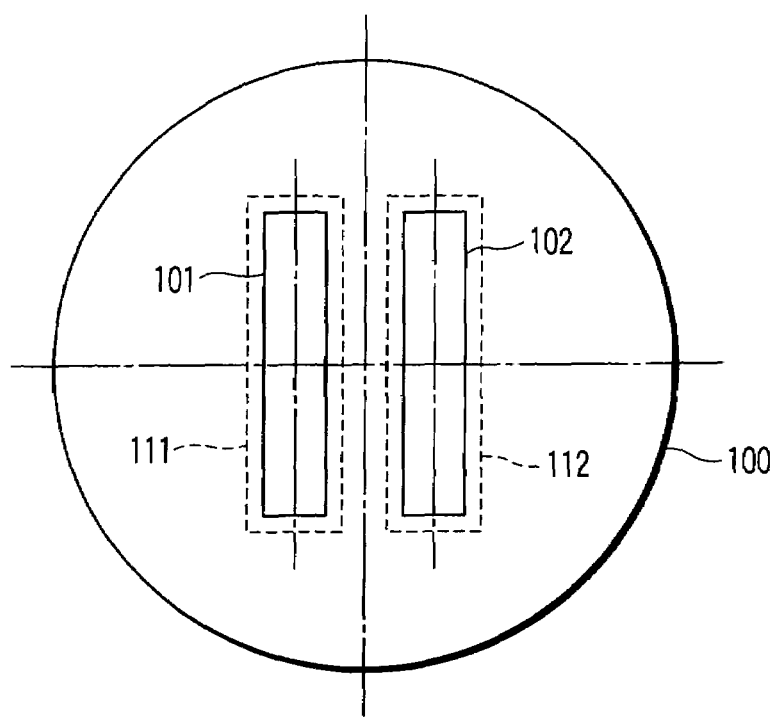
FIG. 4 shows still another example of the positional relationship between the setting positions of the transmission illumination region and reflection illumination region, on one hand, and the setting positions of the visual fields of the imaging sensors, on the other hand.

FIG. 4 shows a position control state with equal priority on transmission and reflection. The center axis of the objective visual field 100 lies between the center axis of the transmission visual field 101 and the center axis of the reflection visual field 102. The distance between the center axis of the transmission visual field 101 and the center axis of the objective visual field 100 is equal to the distance between the center axis of the reflection visual field 102 and the center axis of the objective visual field 100.

Figure 5:
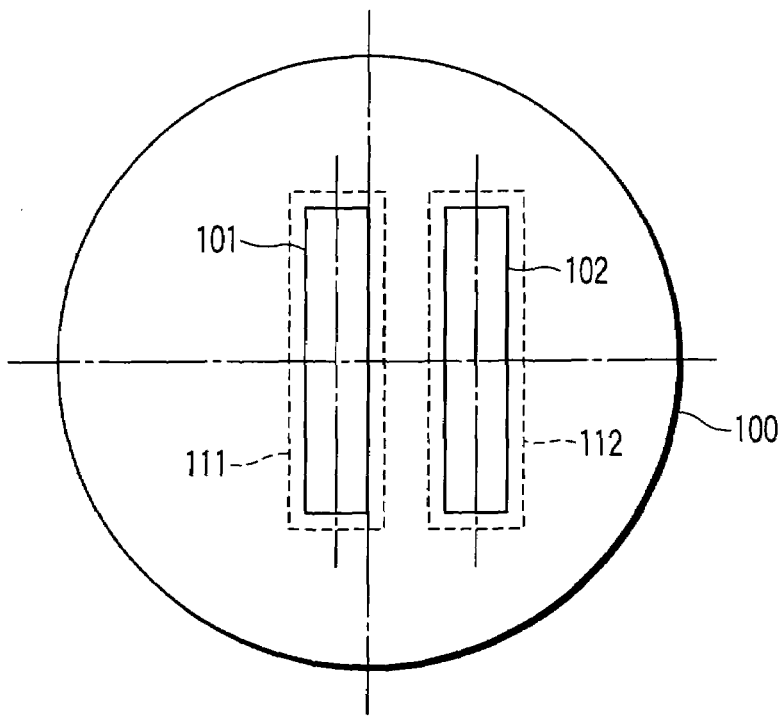
FIG. 5 shows still another example of the positional relationship between the setting positions of the transmission illumination region and reflection illumination region, on one hand, and the setting positions of the visual fields of the imaging sensors, on the other hand.

FIG. 5 shows a position control state which is an intermediate state between the position control state shown in FIG. 2 and the position control state shown in FIG. 4. The center axis of the objective visual field 100 lies between the center axis of the transmission visual field 101 and the center axis of the reflection visual field 102. In addition, the distance between the center axis of the transmission visual field 101 and the center axis of the objective visual field 100 is less than the distance between the center axis of the reflection visual field 102 and the center axis of the objective visual field 100.

Figure 6:
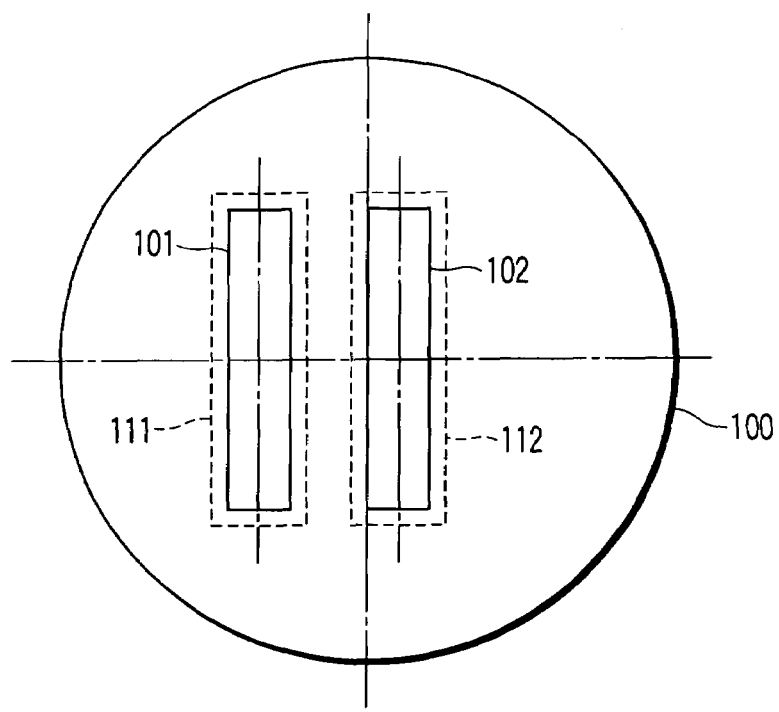
FIG. 6 shows still another example of the positional relationship between the setting positions of the transmission illumination region and reflection illumination region, on one hand, and the setting positions of the visual fields of the imaging sensors, on the other hand.

FIG. 6 shows a position control state which is an intermediate state between the position control state shown in FIG. 3 and the position control state shown in FIG. 4. The center axis of the objective visual field 100 lies between the center axis of the transmission visual field 101 and the center axis of the reflection visual field 102. In addition, the distance between the center axis of the transmission visual field 101 and the center axis of the objective visual field 100 is greater than the distance between the center axis of the reflection visual field 102 and the center axis of the objective visual field 100.

Figure 7:
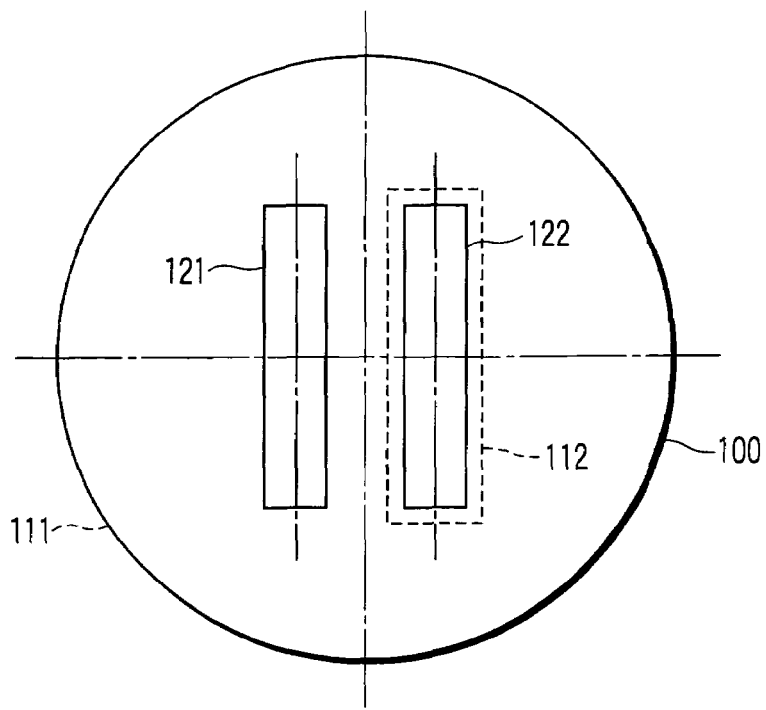
FIG. 7 shows still another example of the positional relationship between the setting positions of the transmission illumination region and reflection illumination region, on one hand, and the setting positions of the visual fields of the imaging sensors, on the other hand.

In the examples of FIG. 2 to FIG. 6, the transmission illumination region 111 and the reflection illumination region 112 are spaced apart from each other. Alternatively, the transmission illumination region 111 and the reflection illumination region 112 may have a common region. FIG. 7 shows an example of this case. In FIG. 7, the transmission illumination region 111 covers the entire objective visual field 100. Accordingly, the visual field (transmission visual field) 121 of the imaging sensor 15 lies within the transmission illumination region 111, and the visual field (transmission/reflection visual field) 122 of the imaging sensor 17 lies within a common region of the transmission illumination region 111 and reflection illumination region 112. For example, the position control state as shown in FIG. 7 can be set by greatly displacing the position of the diaphragm 6 for transmission illumination, which is shown in FIG. 1, from a region of passage of illumination light.

As has been described above, in the present embodiment, there are provided the illumination region position control unit comprising the diaphragm driving mechanisms 23 and 24, and the visual field position control unit comprising the imaging sensor driving mechanisms 25 and 26. The positional relationship between the setting positions of the transmission illumination region and reflection illumination region, on one hand, and the setting positions of the visual fields of the imaging sensors 15 and 17, on the other hand, can be controlled by the illumination region position control unit and the visual field position control unit. Accordingly, various position control states, for example, as shown in FIG. 2 to FIG. 7, can be set, and desired images (images for defect detection) according to purposes can be acquired with high precision. Therefore, with use of the defect inspection apparatus according to the present embodiment, high-precision defect inspections can be performed.

In the above-described embodiment, the diaphragm driving mechanisms 23 and 24 are used as the illumination region position control unit, and the imaging sensor driving mechanisms 25 and 26 are used as the visual field position control unit. Alternatively, the illumination region position and the visual field position may be controlled, for example, by shifting or tilting mirrors, lens, etc. in the optical system.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A defect inspection apparatus comprising:
   an illumination optical system which sets a transmission illumination region and a reflection illumination region on an inspection target surface of a mask;
   first and second imaging units having first and second visual fields which are set on the inspection target surface;
   an imaging optical system that provides images, which are present on the first and second visual fields, on the first and second imaging units;

a defect detection unit which detects a defect of the mask on the basis of the images provided on the first and second imaging units; and a control unit which controls a positional relationship between setting positions of the transmission illumination region and the reflection illumination region and setting positions of the first and second visual fields, the control unit including an illumination region position control unit which controls positions of the transmission illumination region and the reflection illumination region, and a visual field position control unit which controls positions of the first and second visual fields;

wherein the visual field position control unit controls the positions of the first and second visual fields to space the first and second visual fields apart from each other, and wherein the visual field position control unit executes a first position control in which a center axis of the first visual field agrees with a center axis of an objective visual field, a second position control in which a center axis of the second visual field agrees with the center axis of the objective visual field, and a third position control in which the center axis of the objective visual field lies between the center axis of the first visual field and the center axis of the second visual field.

2. The apparatus according to claim 1, wherein the visual field position control unit controls the positions of the first and second visual fields to place the first and second visual fields in the transmission illumination region and the reflection illumination region, respectively.

3. The apparatus according to claim 2, wherein the illumination region position control unit controls the positions of the transmission illumination region and the reflection illumination region to space the transmission illumination region and the reflection illumination region apart from each other.

4. The apparatus according to claim 1, wherein the illumination region position control unit controls the positions of the transmission illumination region and the reflection illumination region to cause the transmission illumination region and the reflection illumination region to have a common region.

5. The apparatus according to claim 1, wherein the illumination optical system includes first and second diaphragms which set the transmission illumination region and the reflection illumination region, respectively.

6. The apparatus according to claim 5, wherein the illumination region position control unit includes mechanisms which move the first and second diaphragms.

7. The apparatus according to claim 1, wherein the visual field position control unit includes mechanisms which move the first and second imaging units.

8. The apparatus according to claim 1, wherein the illumination optical system includes a splitter which separates light from a light source into light for the transmission illumination region and light for the reflection illumination region.

9. The apparatus according to claim 1, wherein the imaging optical system includes a first imaging optical part which guides the image on the first visual field to the first imaging unit, and a second imaging optical part which guides the image on the second visual field to the second imaging unit.

10. The apparatus according to claim 1, wherein the defect detection unit includes a comparison unit which compares the images provided on the first and second imaging units with reference images.

11. The apparatus according to claim 1, wherein the control unit automatically controls the positional relationship.

12. The apparatus according to claim 11, wherein the control unit automatically controls the positional relationship to cause the setting positions of the first and second visual fields to correspond to the setting positions of the transmission illumination region and the reflection illumination region, respectively.

* * * * *